United States Patent [19]

Chen

[11] Patent Number: 5,709,788

[45] Date of Patent: Jan. 20, 1998

[54] DEVICE AND METHOD FOR VERTICAL SLAB GEL CASTING AND ELECTROPHORESIS IN A SINGLE ENCLOSURE

[76] Inventor: Stephen L. Chen, 18510 SW Honeywood Dr., Aloha, Oreg. 97006

[21] Appl. No.: 563,666

[22] Filed: Nov. 25, 1995

[51] Int. Cl.⁶ .................. G01N 27/26; G01N 27/447
[52] U.S. Cl. .................. 204/619; 204/466; 204/467; 204/470; 204/616; 204/618
[58] Field of Search .................. 204/620, 470, 204/456, 457, 458, 459, 461, 462, 463, 464, 465, 466, 467, 468, 469, 606, 607, 608, 609, 610, 616, 618, 619

[56] References Cited

U.S. PATENT DOCUMENTS

| | | | |
|---|---|---|---|
| 4,169,036 | 9/1979 | Anderson et al. | 204/620 X |
| 4,325,796 | 4/1982 | Hoefer et al. | 204/467 |
| 4,576,693 | 3/1986 | Kreisher et al. | 204/620 X |
| 4,652,354 | 3/1987 | Place et al. | 204/470 X |
| 4,784,738 | 11/1988 | Sleeter et al. | 204/470 |
| 4,954,236 | 9/1990 | Kushner et al. | 204/466 |
| 5,047,135 | 9/1991 | Nieman | 204/620 X |
| 5,188,790 | 2/1993 | Magnant | 204/219 |
| 5,192,408 | 3/1993 | Scott | 204/219 |
| 5,472,589 | 12/1995 | Jacobs | 204/620 X |

Primary Examiner—Kathryn L. Gorgos
Assistant Examiner—John S. Starsiak, Jr.

[57] ABSTRACT

A device and method for vertical slab gel casting and electrophoresis in a single enclosure is provided. Air is utilized as a sealing medium to seal the bottom of a gel space for gel casting by constructing an air-tight connection between a sealable lower buffer chamber and a gel space via a junction. The air is automatically released when a buffer is introduce into the lower buffer chamber so that the bottom of the gel is in direct contact with the buffer without manually removing a solid sealing device from the bottom of the gel, which enables the gel to be directly used for electrophoresis without any movement of the gel space.

3 Claims, 1 Drawing Sheet

DEVICE AND METHOD FOR VERTICAL SLAB GEL CASTING AND ELECTROPHORESIS IN A SINGLE ENCLOSURE

BACKGROUND OF THE INVENTION

1. Field of the Invention

The present invention relates to gel casting devices and methods in vertical slab gel electrophoresis.

2. Description of the Prior Arts

Electrophoresis is one of the most commonly utilized tools in biomedical sciences and industries. A key feature of electrophoresis is an utilization of a soft gel matrix. The pore size and shape of the gel matrix is a critical factor for the separation of different components from a mixture. But the pore size and shape of the gel matrix can not stay consistent by itself due to its soft gelatinous features. A pair of glass plates is therefore required for holding the gel matrix. To maintain consistency and uniformity of electrophoresis, an ideal gel matrix should be the one in which an intact gel matrix is directly used for electrophoresis in an apparatus after being casted in a firmly assembled gel space without disturbing the condition of the gel space.

A vertical format of gel electrophoresis is popularly employed because of its convenience in forming a stacking gel and in releasing air bubbles during gel casting. The liquid gel solution in vertical gel space, however, exhibits an inherent tendency of leakage due to a gravity action. Thus, the bottom, as well as two vertical sides, of the gel space must be securely sealed with a liquid impermeable sealing device. The sealing device then has to be manually removed from the bottom of the gel space for conducting electric current across the gel matrix inan electrophoresis apparatus.

Many attempts have been made for improving gel casting device and method. U.S. Pat. No. 4,784,738 Sleeter et al., for example, teaches a wettable membrane which is prewetted with gel solution to seal the bottom of gel space, U.S. Pat. No. 4,954,236 Kushner et al. teaches a flexible sealing sheet with a removable edge to seal the bottom of gel space, U.S. Pat. No. 5,188,790 Magnant teaches a rectangular liquid impermeable bag to seal the bottom of the gel space, and U.S. Pat. No. 5,192,408 Scott teaches a sealing gasket to seal the bottom of the gel space. These prior arts, while creating some differences from each other, are all limited in a scope of a classic convention, that is, (1) a solid, liquid impermeable device has to be placed at the bottom of the gel space in direct contacting with gel solution, and (2) the sealing device has to be manually removed from the bottom of the gel space before using the gel matrix for electrophoresis. Within the limited concept, an extended procedure of handling is unavoidable. The disappointing side of the extended procedure is that the handling of the casted gel matrix itself does not improve the performance of the gel matrix but rather disturbing the consistency and uniformity of the gel matrix.

The reality of gel casting devices and methods remains in an unsatisfactory situation far away from ideal.

SUMMARY OF THE INVENTION

It is, thereafter, an object of the present invention to provide an improved device and method for vertical slab gel casting and gel electrophoresis, an improvement in simplifying the procedure of handling and an improvement in providing an intact gel matrix for direct using in electrophoresis without disturbance to the gel space. The advantages of the invention are:

1. The consistence and the uniformity of the gel matrix are improved by using the casted gel matrix directly for electrophoresis without either manually removing a solid sealing device from gel bottom or relocating the gel space.
2. The procedure of operation is simplified by omitting all unnecessary manipulations.
3. High security of leak-proof is established by using a force-enhancing fastening device and using the flat side of glass plates as a sealing surface.

DETAILED DESCRIPTION OF THE INVENTION

Figure 1:
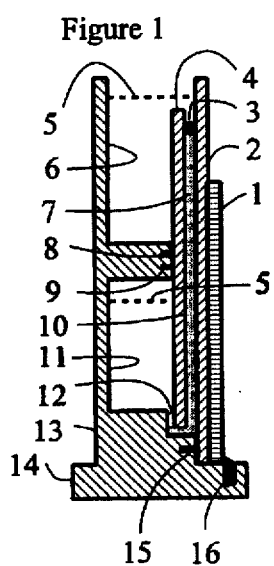
FIG. 1 is a cross-sectional view of a device according to the invention.
Figure 2:
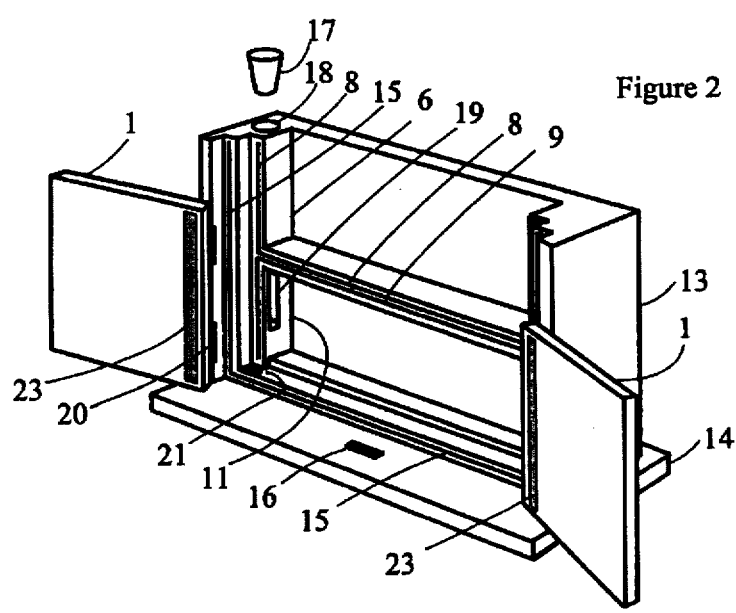
FIG. 2 is a perspective view of the device of FIG. 1 with two glass plates being removed.
Figure 3:
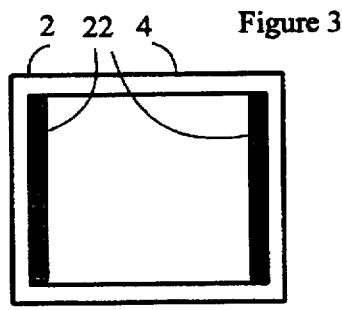
FIG. 3 is a from-side view of the two glass places being removed from FIG. 2.
Figure 4:
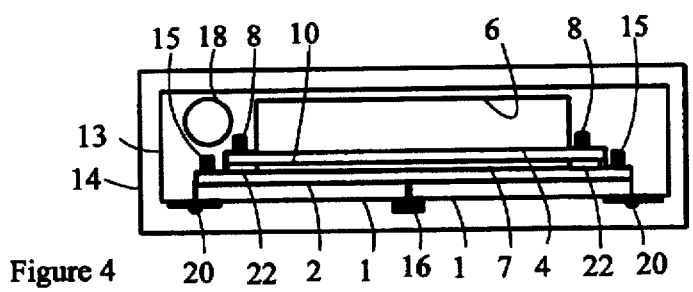
FIG. 4 is a top-side view of the device of FIG. 1 with the two glass plates being placed.

A gel space 10 for gel casting is assembled by a first glass plate 4, a second glass plate 2, and two spacers 22. The bottom of gel space 10 is connected to a lower buffer chamber 11 via an air-tight junction 12. An inlet 18 of lower buffer chamber 11 is sealable so that air in lower buffer chamber 11 can be utilized as a sealing medium for sealing the bottom of gel space 10.

The operation procedure of the device and method is as follows:

First glass plate 4 is placed against a sponge cord 8 and a sponge cord 9 on a body 13.

Two spacers 22 are placed against first glass plate 4 at two vertical sides respectively.

Second glass plate 2 is placed against two spacers 22 on first glass plate 4.

Two fastening doors 1 are closed and a rubber stopper 17 is placed into inlet 18.

A gel forming solution is introduced into gel space 10 to form a gel matrix 7.

Rubber stopper 17 is removed from inlet 18 after forming gel matrix 7.

A buffer 5 is introduced into an upper buffer chamber 6 and lower buffer chamber 11.

A sample 3 is loaded onto gel matrix 7.

A electrical potential is impressed between buffer 5 in upper buffer chamber and buffer 5 in lower buffer to cause electrophoresis of sample 3.

The mechanism of the device and method is as follows:

An air-tight structure is designed between lower buffer chamber 11 and gel space 10 via junction 12. Sponge cord 8 seals the upper portion of first glass plate 4 to upper buffer chamber 6. Sponge cord 9 seals the lower portion of first glass plate 4 to lower buffer chamber 11. A thin gap remains between the bottom of first glass plate 4 and the bottom of lower buffer chamber 11 as junction 12. Two miniblocks 21 elevate the bottom of first glass plate 4 to maintain junction 12 at 1.5 mm thickness. Sponge cord 15 is constructed at a level lower than that of junction 12 on body 13 so that an air-tight connection between lower buffer chamber 11 and gel space 10 is built. When casting a gel, the gel forming solution should flow into lower buffer chamber 11 from gel space 10 via junction 12. But the air in lower buffer chamber 11 has no way to escape when inlet 18 is sealed by rubber stopper 17. An increasing air pressure in lower buffer chamber 11 exists a resistant force on incoming gel forming solution so that the gel forming solution stays in gel space 10 as if the bottom of gel space 10 were sealed. Junction 12, being designed at a level lower than that of both the bottom of lower buffer chamber 11 and the bottom of gel space 10, prevents air from escaping into gel space 10 and minimizes the amount of incoming gel forming solution to a negligible level.

Unlike those prior arts, the material used as a sealing medium in direct contacting with the bottom of gel matrix is an air, rather than a solid device. The air is automatically released when introducing buffer 5 into lower buffer chamber 11 without manually removing a solid sealing device from the bottom of gel space 10. Buffer 5 now is in contacting with gel matrix 7 so that gel matrix 7 in gel space 10 can be directly used for electrophoresis, which ensures an intact condition of gel matrix 7.

Other features of the device are as follows:

Upper buffer chamber 6 and lower buffer chamber 11 have only three permanent vertical walls respectively. First glass plate 4 is utilized as the fourth vertical wall of upper buffer chamber 6, the fourth wall of lower buffer chamber 11, and the wall of gel space simultaneously. This design offers an excellent even heat distribution because of first glass plate 4 is evenly immersed in buffer 5. An uniform migration rate of samples is obtained across all positions of gel matrix 7.

First glass plate 4 and second glass plate 2 have thickness of 6 ram. The dimension of width of second glass plate 2 is 1.5 cm wider than that of first glass plate 4 and the dimension of height of second glass plate 2 is 2.5 cm higher than that of first glass plate 4. When placing on body 13, the bottom of second glass plate 2 is 7 mm lower than the bottom of first glass plate 4.

For an easy observation of well forming and sample loading without obscurity, a clear visibility of sample wells is designed by placing upper portion of gel space 10 at an outmost position over a clear background.

A force-enhancing structure, fastening doors 1, is employed for an easy operation. The adjacent edge of fastening door 1 near hinges 20 exports a potent force on second glass plate 2 evenly when the remote edge of fastening door 1 is lightly closed. When two fastening doors 1 are closed, a fastening force is imposed on second glass plate 2, spacers 22, and first glass plate 4. High security of leak-proof is accomplished by using the flat side of glass plates, rather than using the edge, as a sealing surface, which eliminates the problem of leakage caused by damaged edge or by improper alignment. The security is further enforced when the sealing is fastened by fastening doors 1.

A slot 19 connects inlet 18 to lower buffer chamber 11 for introducing buffer 5.

A lock 16, with a spring inside in base 14, is able to lock fastening doors 1 automatically when fastening doors 1 are pushed pass it. Fastening doors 1 can be opened when lock 16 is pressed down. A flexibility of pads 23 on fastening doors 1 and of sponge cords on body 13 allows changes of spacers 22 in different thickness.

Sponge cord 8 is arranged in an "U" shape along upper buffer chamber 6. Sponge cord 15 is also arranged in an "U" shape. Sponge cord 9 is arranged in an upside down "U" shape along the lower buffer chamber 11. All sponge cords are replaceable.

Although the description above contains specifications, it will apparent to those skilled in the art that a number of other variations and modifications may be made in this invention without departing from its spirit and scope. A sealing cover, for example, can be used for sealing inlet 18, a rubber sheet can be used for sealing glass plates to body, a clamp can be used as a fastening means, two spacers can be attached to one of the glass plates, the procedure of placing rubber stopper 17 can be set as the first step in a gel casting before placing first glass plate 4 on body. Thus, the description as set out above should not be constructed as limiting the scope of the invention but as merely providing illustration of one of the presently preferred embodiment of the invention.

What is claimed is:

1. An device for gel casting and gel electrophoresis in a single enclosure, comprising a first plate and a second plate in rectangular shape at a substantially upright position, said second plate having a size greater than that of said first plate and placed in parallel with said first plate;

two spacers, placed between said first plate and said second plate along two upright sides of said first plate, separating said first plate from said second plate;

a gel space, defined by said first plate, said second plate, and said two spacers, having an open top, and an open bottom;

an upper buffer chamber having a shelf as bottom and three substantially upright walls, a fourth upright wall of said upper buffer chamber being constructed by an upper portion of said first plate, said upper buffer chamber having buffer communication with said gel space via said open top of said gel space;

a lower buffer chamber, located underneath said upper buffer chamber, having said shelf as top, a stepped base as bottom, and three substantially upright walls, a lower portion of said first plate being constructed as a fourth upright wall of said lower buffer chamber, said lower buffer chamber having buffer communication with said gel space via said open bottom of said gel space;

an inlet of said lower buffer chamber being sealable by a first sealing member to set said lower buffer chamber as a closed chamber for creating a back pressure in said lower buffer chamber to oppose movement of a gel forming solution out of said gel space through said open bottom of said gel space;

a second sealing member located between said upper portion of said first plate and said upper buffer chamber along an edge of said shelf and two stepped edges of said three substantially upright walls of said upper buffer chamber, said second sealing member sealing said first plate to said upper buffer chamber;

a third sealing member located between said lower portion of said first plate and said lower buffer chamber along said edge of said shelf and two stepped edges of said three substantially upright walls of said lower buffer chamber, said third sealing member sealing said first plate to said lower buffer chamber;

a fourth sealing member located between said second plate and both of said upper buffer chamber and said lower buffer chamber along an edge of said stepped base and said two stepped edges of said three substantially upright walls of both of said upper buffer chamber and said lower buffer chamber, said fourth sealing member sealing said second plate to both of said upper buffer chamber and said lower buffer chamber; and a fastening member pressing both of said first plate and said second plate against both of said upper buffer chamber and said lower buffer chamber to secure sealing.

2. The device of claim 1 wherein said second plate is both longer and wider than that of said first plate.

3. A method of performing gel casting and gel electrophoresis, comprising the steps of:

(a) providing a first plate and a second plate in rectangular shape at a substantially upright position, said second plate having a size greater than that of said first plate and placed in parallel with said first plate;

two spacers, located between said first plate and said second plate along two upright sides of said first plate, separating said first plate from said second plate;

a gel space, defined by said first plate, said second plate, and said two spacers, having an open top, and an open bottom;

an upper buffer chamber having a shelf as bottom and three substantially upright walls, a fourth upright wall of said upper buffer chamber being constructed by an upper portion of said first plate, said upper buffer chamber having buffer communication with said gel space via said open top of said gel space;

a lower buffer chamber, located underneath said upper buffer chamber, having said shelf as top, a stepped base as bottom, and three substantially upright walls, a lower portion of said first plate being constructed as a fourth upright wall of said lower buffer chamber, said lower buffer chamber having buffer communication with said gel space via said open bottom of said gel space;

an inlet of said lower buffer chamber being sealed by a first sealing member to set said lower buffer chamber as a closed chamber for creating a back pressure in said lower buffer chamber to oppose movement of a gel forming solution out of said gel space through said open bottom;

a second sealing member located between said upper portion of said first plate and said upper buffer chamber along an edge of said shelf and two stepped edges of said three substantially upright walls of said upper buffer chamber, said second sealing member sealing said first plate to said upper buffer chamber;

a third sealing member located between said lower portion of said first plate and said lower buffer chamber along said edge of said shelf and two stepped edges of said three substantially upright walls of said lower buffer chamber, said third sealing member sealing said first plate to said lower buffer chamber;

a fourth sealing member located between said second plate and both of said upper buffer chamber and said lower buffer chamber along an edge of said stepped base and said two stepped edges of said three substantially upright walls of both of said upper buffer chamber and said lower buffer chamber, said fourth sealing member sealing said second plate to both of said upper buffer chamber and said lower buffer chamber; and a fastening member pressing both of said first plate and said second plate against both of said upper buffer chamber and said lower buffer chamber to secure sealing.

(b) introducing said gel forming solution into said gel space, said gel forming solution being held in said gel space and prevented from entering said lower buffer chamber through said open bottom of said gel space by said back pressure in said lower buffer chamber;

(c) allowing said gel forming solution to form a gel matrix in said gel space;

(d) unsealing said inlet of said lower buffer chamber to establish a buffer communication between said lower buffer chamber and ambient environment;

(e) introducing a buffer into both of said upper buffer chamber and said lower buffer chamber to immerse said open top and said open bottom of said gel space;

(f) applying a sample to be electrophoresed to said gel matrix in said gel space; and (g) impressing an electrical potential to said buffer in both of said upper buffer chamber and said lower buffer chamber to cause electrophoresis of said sample.

* * * * *